United States Patent
Roberts et al.

(10) Patent No.: US 9,724,178 B2
(45) Date of Patent: Aug. 8, 2017

(54) WATER FLOSSER TIP HAVING A CONTAINER FOR TREATMENT TABLETS

(71) Applicants: David Michael Roberts, San Marcos, CA (US); Ronald Edward Welch, San Marcos, CA (US)

(72) Inventors: David Michael Roberts, San Marcos, CA (US); Ronald Edward Welch, San Marcos, CA (US)

( * ) Notice: Subject to any disclaimer, the term of this patent is extended or adjusted under 35 U.S.C. 154(b) by 43 days.

(21) Appl. No.: 14/670,131

(22) Filed: Mar. 26, 2015

(65) Prior Publication Data
US 2015/0282909 A1    Oct. 8, 2015

Related U.S. Application Data

(60) Provisional application No. 61/974,379, filed on Apr. 2, 2014.

(51) Int. Cl.
*A61C 7/02* (2006.01)
*A61C 17/02* (2006.01)
*A61C 19/06* (2006.01)

(52) U.S. Cl.
CPC ........ *A61C 17/0202* (2013.01); *A61C 19/063* (2013.01)

(58) Field of Classification Search
CPC ..... A61C 17/02; A61C 17/0202; A61C 15/00; A61C 19/063; A61C 1/0084; A61C 1/087
USPC ..................................................... 433/80, 88
See application file for complete search history.

(56) References Cited

U.S. PATENT DOCUMENTS

| | | | |
|---|---|---|---|
| 2007/0080240 A1 | 4/2007 | Schuetz | |
| 2009/0075231 A1* | 3/2009 | Tontz | A61C 19/06 433/88 |
| 2010/0151406 A1* | 6/2010 | Boutoussov | A61C 1/0046 433/29 |
| 2012/0141953 A1* | 6/2012 | Mueller | A61C 3/025 433/88 |
| 2012/0183926 A1 | 7/2012 | Shalev | |
| 2012/0282570 A1 | 11/2012 | Mueller | |

FOREIGN PATENT DOCUMENTS

WO    2008046580 A1    4/2008

* cited by examiner

*Primary Examiner* — Allen Porter, Jr.
(74) *Attorney, Agent, or Firm* — Donn K. Harms

(57) ABSTRACT

Some embodiments of the present disclosure include a water flosser handle for providing treatment deep into a user's gum pockets. The water flosser handle may include a chamber configured to hold a treatment tablet, a flosser tip attached to a distal end of the handle, and a water supply tube attached to a proximal end of the handle. The handle may be configured to allow passage of pressurized water therethrough into a user's mouth. A treatment tablet may be positioned within the chamber such that the water pressure of the water configured to flow through the handle at least partially dissolves and transports the treatment tablet into the user's mouth and gums.

7 Claims, 4 Drawing Sheets

FIG.1
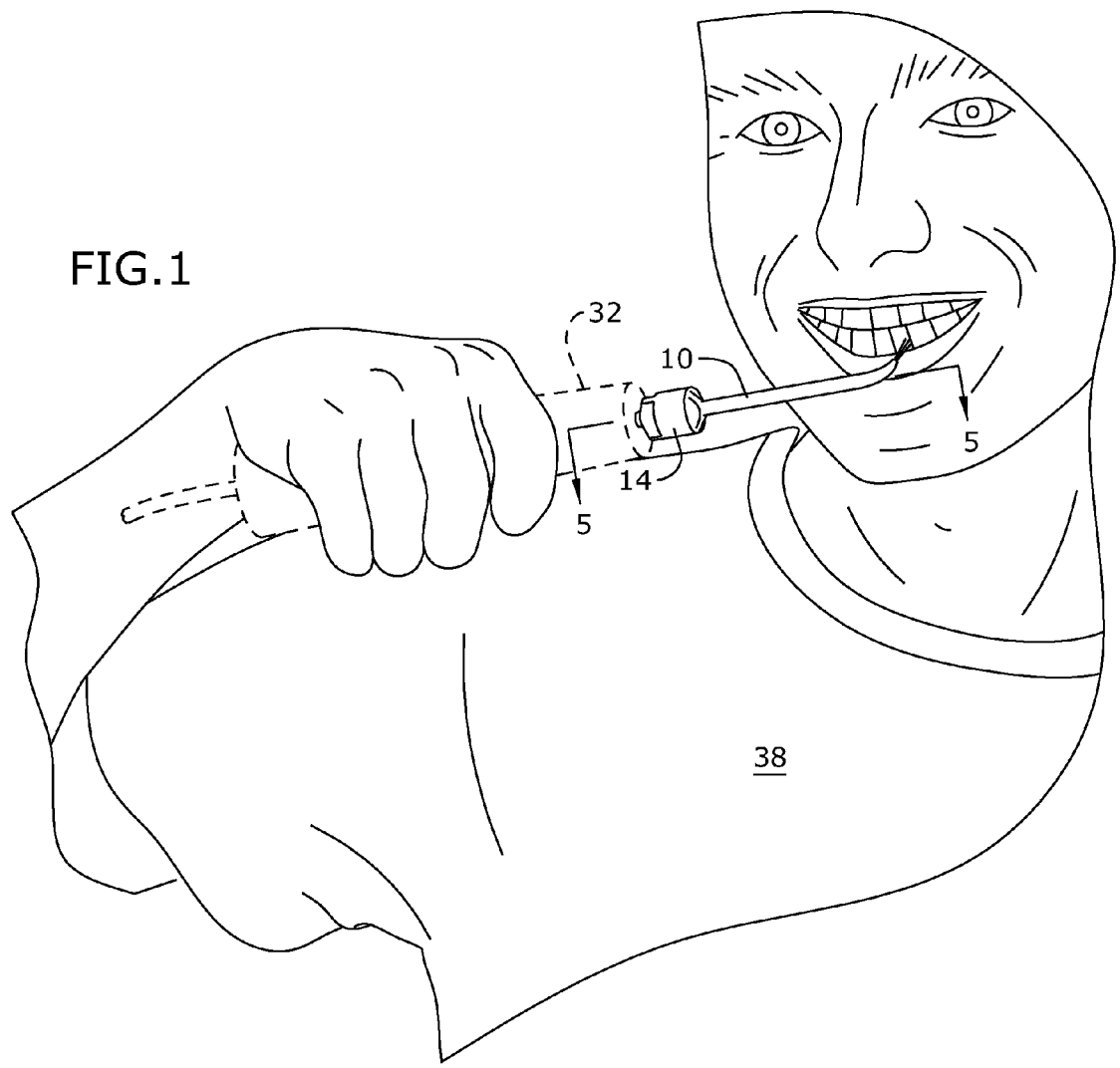
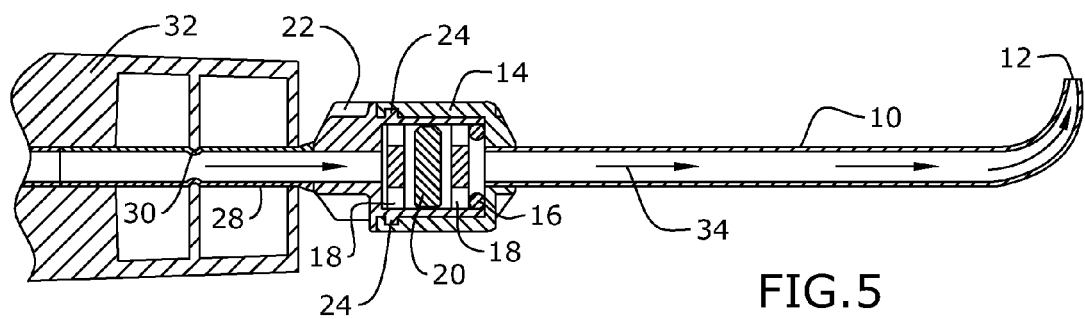
FIG.5

US 9,724,178 B2

WATER FLOSSER TIP HAVING A CONTAINER FOR TREATMENT TABLETS

RELATED APPLICATION

This application claims priority to provisional patent application U.S. Ser. No. 61/974,379 filed on Apr. 2, 2014, the entire contents of which is herein incorporated by reference.

BACKGROUND

The embodiments described herein relate generally to dental accessories, and more particularly, to a water flosser having a container for a tablet.

Brushing your teeth with a toothbrush and flossing your teeth with dental floss is not sufficient for deep cleaning the areas between your teeth. Thus, a lot of people use water flossers to clean the areas between their teeth. However, conventional water flossers simply pass pressurized water through the device to clean the areas between your teeth and do not include a convenient way to provide treatment deep into the gum pockets to address periodontal diseases.

Therefore, what is needed is a water flosser capable of providing treatment deep into gum pockets.

SUMMARY

Some embodiments of the present disclosure include a water flosser handle for providing treatment deep into a user's gum pockets. The water flosser handle may include a chamber configured to hold a treatment tablet, a flosser tip attached to a distal end of the handle, and a water supply tube attached to a proximal end of the handle. The handle may be configured to allow passage of pressurized water therethrough into a user's mouth. A treatment tablet may be positioned within the chamber such that the water pressure of the water configured to flow through the handle at least partially dissolves and transports the treatment tablet into the user's mouth and gums.

BRIEF DESCRIPTION OF THE FIGURES

The detailed description of some embodiments of the invention is made below with reference to the accompanying figures, wherein like numerals represent corresponding parts of the figures.

FIG. 1 is a perspective view of one embodiment of the present invention, shown in use.

FIG. 5 is a section view of one embodiment of the present invention, taken along line 5-5 in FIG. 1.

DETAILED DESCRIPTION OF CERTAIN EMBODIMENTS

Figure 2:
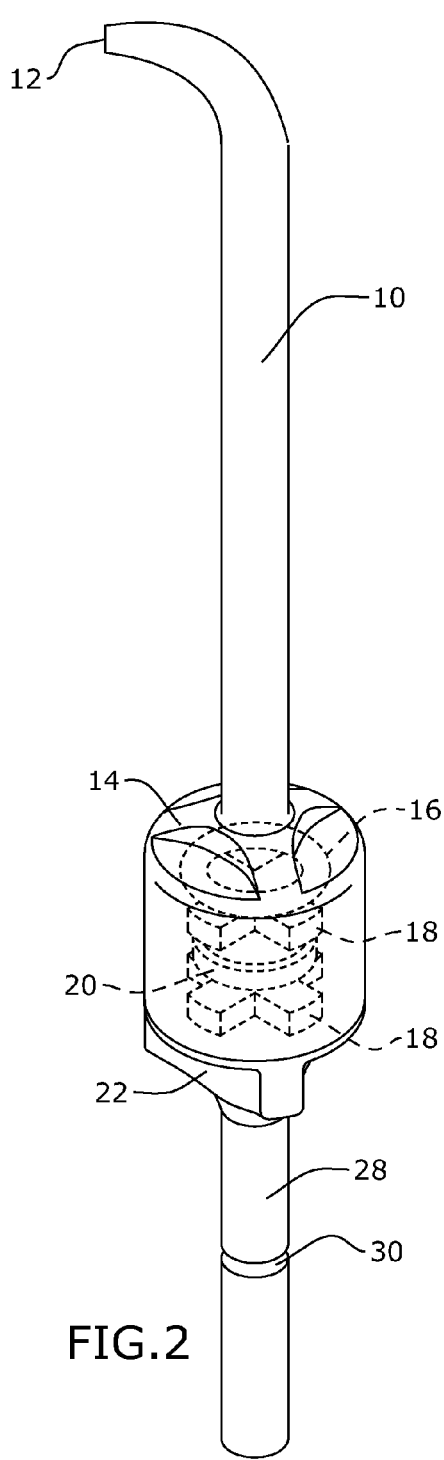
FIG. 2 is a perspective view of one embodiment of the present invention.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to provide treatment deep into the gum pockets of a user and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Water Flosser Handle
2. Treatment Cavity or Chamber

The various elements of the water flosser for providing a treatment to a user's gum pockets of the present disclosure may be related in the following exemplary fashion. It is not intended to limit the scope or nature of the relationships between the various elements and the following examples are presented as illustrative examples only.

By way of example, and referring to FIGS. 1-8, some embodiments of the invention include a water flosser handle for providing treatment deep into a user's gum pockets, the water flosser handle comprising a chamber configured to hold a treatment tablet 20, a flosser tip 10 attached to a distal end 14 of the handle, and a water supply tube 28 attached to a proximal end 22 of the handle, wherein the handle is configured to allow passage of pressurized water therethrough into a user's mouth, and the treatment tablet 20 is positioned within the chamber such that the water pressure of the water configured to flow through the handle at least partially dissolves and transports the treatment tablet into 20 the user's mouth and gums.

Figure 3:
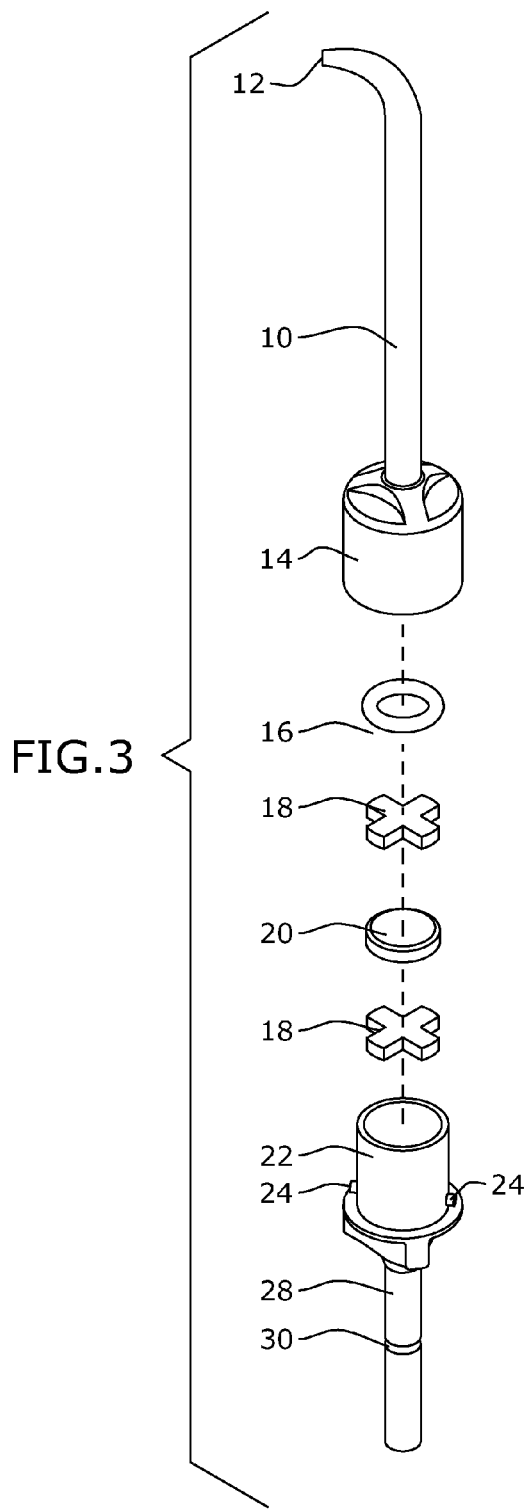
FIG. 3 is an exploded view of one embodiment of the present invention.
Figure 4:
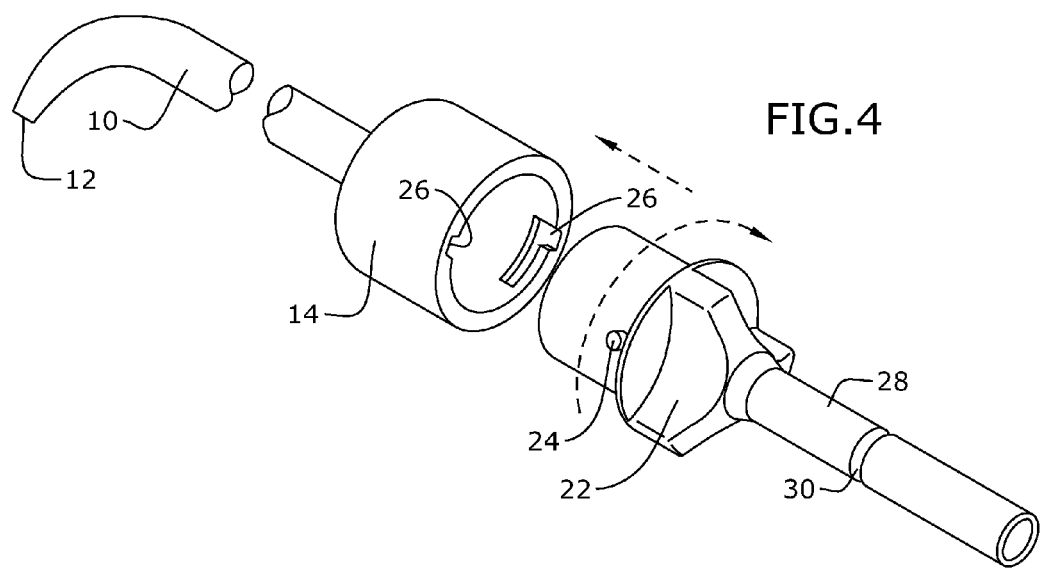
FIG. 4 is an exploded view of one embodiment of the present invention.
Figure 6:
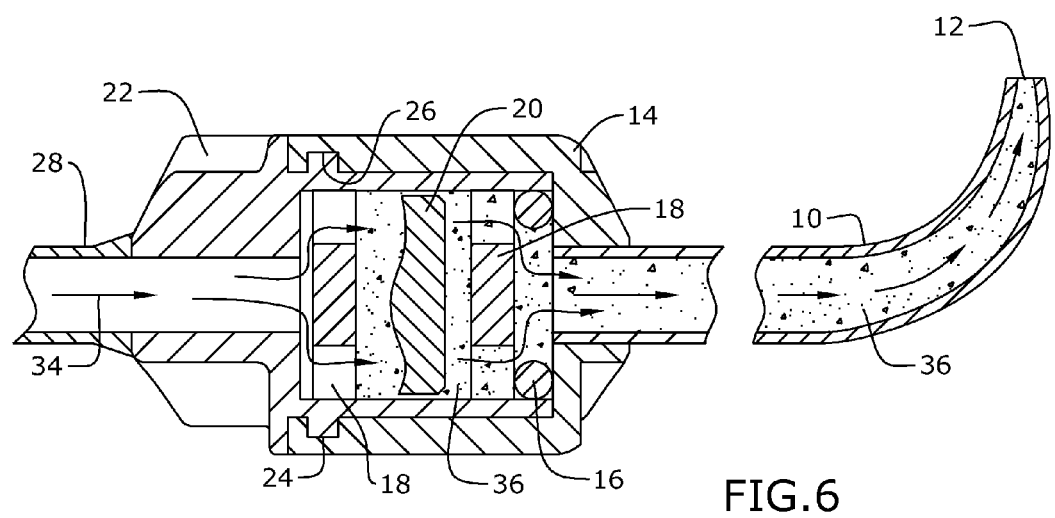
FIG. 6 is an enlarged section view of one embodiment of the present invention.
Figure 7:
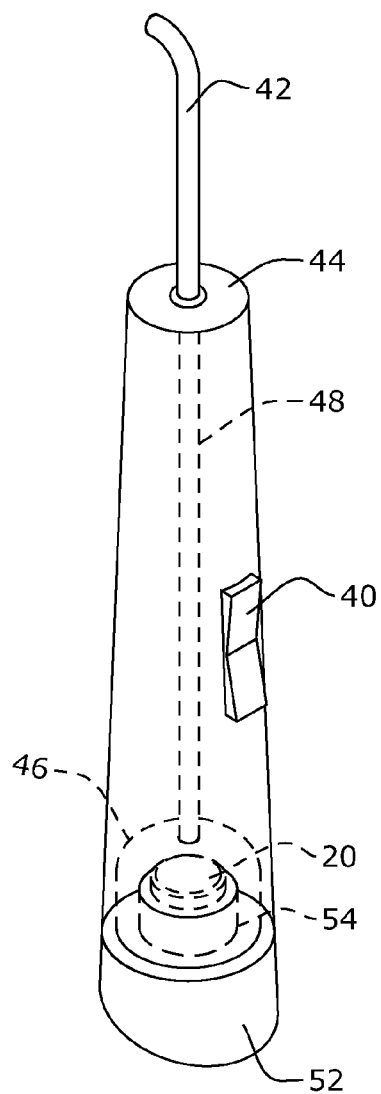
FIG. 7 is a perspective view of one embodiment of the present invention.
Figure 8:
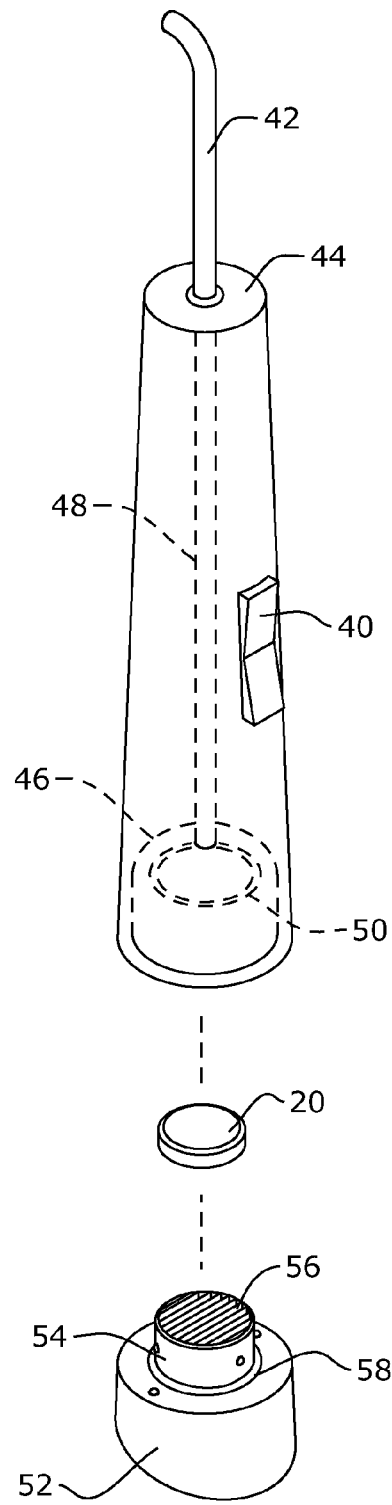
FIG. 8 is a perspective view of one embodiment of the present invention.

As shown in FIGS. 1-6, some embodiments of the water flosser handle comprise a tip 10 extending from an distal end 14, a proximal end 22 removably attached to the distal end 14, the proximal end 22 comprising a cavity or chamber configured to hold a treatment, such as a treatment in tablet form 20, and a water supply tube 28 extending from the proximal end 22, the water supply tube 28 configured to removably attach to a conventional water flosser 32. The distal end 14 and the proximal end 22 may be removably attached using any conventional connecting mechanism, so long as a watertight seal is formed between the distal end 14 and the proximal end 22. For example, in some embodiments, the proximal end 22 comprises at least one lock knob 24 configured to engage with at least one lock knob slot 26 in the distal end 14. When the lock knob 24 is inserted into the lock knob slot 26 and the distal end 14 is rotated, the distal end 14 and the proximal end 22 may be connected with a watertight seal. Also, as shown in FIGS. 2 and 3, the chamber walls of the proximal end 22 may have such a size that they can be enveloped by the distal end 14.

Embodiments of the device may also comprise additional elements positioned within the chamber of the proximal end 22. For example, a pair of diffusers 18 (or screens) also be positioned within the chamber, such that the tablet 20 is sandwiched between the two diffusers 18. The diffusers 18 may slow down the rate of dissolution of the tablet 20 when the device is in use. Additionally, an O-ring 16 may be placed above the top diffuser 18, such that the O-ring is positioned between the diffuser 18 and the distal end 14, as shown in FIGS. 2 and 3.

As mentioned above, and as shown in FIG. 5, the proximal end 22 may have a water supply tube 28 extending therefrom, wherein the water supply tube 28 may be configured to engage with a conventional water flosser 32, such that the device of the present disclosure may replace the use of a conventional water flosser tip. For example, the water supply tube 28 may comprise a water supply tube lock notch 30 configured to engage with a ridge in the water flosser 32, wherein water 34 is configured to flow from the water flosser 32, through the water supply tube 28, through the chamber, and finally through the tip and an orifice in the tip end 12 into the mouth of a user 38. The pressure of the water 34 may aid in dissolving and transporting the treatment tablet 20 through the tip 10 and into a user's gum pockets.

Other embodiments of the water flosser handle may comprise a larger, alternate distal end 44 removably attached to an alternate proximal end 52, wherein the alternate distal end 44 comprises a water tube 48 through which water may flow, and an alternate chamber 46 that has an opening on a bottom surface of the alternate distal end 44, which is configured to engage with a stand 54 attached to the alternate proximal end 52. The alternate chamber 46 may comprise an upper gasket 50, which only allows small pieces of the tablet 20 to flow through the remainder of the alternate distal end 44. The stand 54 may have a grate 56 through which water is capable of flowing. A proximal end of the stand 54 may comprise a lower gasket 58 configured to create a watertight seal between the alternate distal end 44 and the alternate proximal end 52 when the alternate distal end 44 is removably attached to the alternate proximal end 52. To use this embodiment of the water flosser, a user 38 may place the tablet 20 on the tablet stand 54 and attach the alternate distal end 44 to the alternate proximal end 52. The user 38 may then turn the water flosser on by, for example, switching a switch 40 to the "on" position, starting the flow of water through the device. The water may flow through the grate 56 in the stand 54 on the alternate proximal end 52 into the alternate chamber 46. The pressure of the water may aid in dissolving and transporting the tablet 20 through the water tube 48 into the flosser tip 42 and into the mouth and, particularly, the gum pockets of a user 38.

In yet further embodiments, the cavity or chamber configured to hold a treatment, for instance a treatment in tablet form, may be located at any other position throughout the handle of the water flosser, such as in the lower handle.

It embodiments, the treatment may be a partially or completely dissolvable tablet. The tablet may contain any desired treatment for aiding in cleaning the mouth and preventing periodontal diseases. For example, the tablet may be mouthwash in tablet form or the tablet may comprise other treatments, such as fluoride, that may aid in the prevention of gum or dental diseases and may combat bad breath. In some embodiments, the tablets may be flavored to encourage people, such as children, to use the tablets. For example, the tablets may be mint-, bubble gum-, or fruit-flavored.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A water flosser tip, comprising:
    an elongated tip, said elongated tip extending between a tip end having an orifice therein, to an opposite end;
    an axial passage running through said elongated tip, from said orifice to a distal end of a chamber connected to said elongated tip at said opposite end thereof;
    a supply tube having a passage therethrough, said passage in a sealed connection with a proximal end of said chamber at a first end of said supply tube, said passage extending to a distal end of said supply tube;
    said distal end of said supply tube adapted for engagement with a pressurized water supply; and
    said chamber configured with a pair of diffusers positioned within the chamber, said diffusers adapted to hold said tablet in a sandwiched position in-between said pair of diffusers, such that the pressurized water supply flowing through said passage from said distal end of said supply tube and discharging into said proximal end of said chamber, partially dissolves and transports dissolved portions of said treatment tablet to said axial passage at said distal end of said chamber and into the user's mouth and gums through said orifice at said tip end.

2. The water flosser tip of claim 1, further comprising said supply tube having a tube lock notch configured to engage with a ridge in a water flosser.

3. The water flosser tip of claim 1 further comprising:
    a removable engagement between said proximal end and said distal end of said chamber; and
    said treatment tablet positionable within said chamber by disengagement of said removable engagement to provide access to said chamber.

4. The water flosser tip of claim 2 further comprising:
    a removable engagement between said proximal end and said distal end of said chamber; and
    said treatment tablet positionable within said chamber by disengagement of said removable engagement to provide access to said chamber.

5. The water flosser tip of claim 1, further comprising said supply tube having a tube lock notch configured to engage with a ridge in a water flosser.

6. The water flosser tip of claim 5 further comprising:
    a removable engagement between said proximal end and said distal end of said chamber; and
    said treatment tablet positionable within said chamber by disengagement of said removable engagement to provide access to said chamber.

7. The water flosser tip of claim 1 further comprising:
    a removable engagement between said proximal end and said distal end of said chamber; and
    said treatment tablet positionable within said chamber by disengagement of said removable engagement to provide access to said chamber.

\* \* \* \* \*